(12) United States Patent
Levy

(10) Patent No.: US 6,251,608 B1
(45) Date of Patent: Jun. 26, 2001

(54) METHOD OF DETERMINING A POTENTIAL OF A HYPERGLYCEMIC PATIENTS OF DEVELOPING VASCULAR COMPLICATIONS

(75) Inventor: Andrew P. Levy, Kiryat Shmuel (IL)

(73) Assignee: Technion Research & Development Foundation, Ltd., Haifa (IL)

( * ) Notice: Subject to any disclaimer, the term of this patent is extended or adjusted under 35 U.S.C. 154(b) by 0 days.

(21) Appl. No.: 09/556,469

(22) Filed: Apr. 20, 2000

(51) Int. Cl.[7] ............... C12Q 1/68; C07H 21/04; C12P 19/34; G01N 33/53
(52) U.S. Cl. ............... 435/6; 536/23.1; 435/91.2; 435/91.52; 435/7.1
(58) Field of Search .................. 435/6, 91.2, 91.52, 435/7.1; 536/23.1

(56) References Cited

PUBLICATIONS

Gugliucci "Glycation as the glucose link to diabetic complications" J. Am. Osteopath. Assoc. vol. 100, No. 10, p. 621–634, Oct. 2000 (abstract only).*

Nishikawa et al. "The missing link: A single unifying mechanism for diabetic complications" Kidney Int. vol. 58, p. 26–30, Sep. 2000 (abstract only).*

Chandra et al "Haptoglobin Phenotypes in Diabetes mellitus and Diabetic Retinography" Hum. Hered. vol. 41, p. 347–350, 1991.*

Delanghe et al "Haptoglobin polymorphism and peripheral arterial occlusive disease" Atherosclerosis, vol. 145, p. 287–292, 1999.*

Langlois et al "Biological and clinical significance of haptoglobin polymorphism in humans" Clinical Chemistry, vol. 42, No. 10, p. 1589–1600, 1996.*

Prabha et al "Haptoglobin patterns in essential hypertension and associated conditions—increase risk for Hp (2–2)" Hum Hered. vol. 37, p. 345–348, 1987.*

\* cited by examiner

*Primary Examiner*—Lisa B. Arthur
*Assistant Examiner*—Jeanine Goldberg

(57) ABSTRACT

Methods for determining a potential of a hyperglycemic patient to develop vascular complications in response to oxidative stress and for determining the importance of reducing oxidative stress in a specific hyperglycemic patient are disclosed. Each method includes the step of determining a haptoglobin phenotype of the patient. A variety of means of making this determination are further disclosed.

14 Claims, 2 Drawing Sheets

METHOD OF DETERMINING A POTENTIAL OF A HYPERGLYCEMIC PATIENTS OF DEVELOPING VASCULAR COMPLICATIONS

FIELD AND BACKGROUND OF THE INVENTION

The present invention relates to a method of determining the importance of reducing oxidative stress in a specific hyperglycemic patient, and further to a method of determining a potential of a hyperglycemic patient to develop vascular complications in response to oxidative stress. More particularly, the present invention relates to determining a haptoglobin phenotype of a hyperglycemic patient as a means of predicting the likelihood of the patient developing vascular complications related to oxidative stress. More particularly, the present invention further relates to determining a haptoglobin phenotype of a hyperglycemic patient as a means of evaluating the potential efficacy of antioxidant therapy as an adjunct to treatment for a hyperglycemic patient.

Haptoglobin (Hp) is a hemoglobin-binding serum protein which plays a major role in the protection against heme-driven oxidative stress (Langlois M R and Delanghe J R (1996) Clin Chem 42: 1589–1600; Delanghe J R et al. (1998) AIDS 12: 1027–1032; Gutteridge J M. (1987) Biochim Biophys Acta 917: 219–223; Miller Y I et al. (1997) Biochem 36: 12189–12198; Vercellotti G M et al. (1994) Art Cell Blood Substit Imm Biotech 22: 207–213). Mice lacking the Hp gene demonstrate a dramatic increase in oxidative stress and oxidative tissue damage particularly in the kidney (Lim S K et al., (1998) Blood 92: 1870–1877).

In man, there are two common alleles for Hp (1 and 2) manifesting as three major phenotypes 1-1, 2-1 and 2-2 (Bowman B H and Kurosky A. (1982) Adv Hum Gen 12: 189-26).

Functional differences in the hemoglobin-binding capacity of the three phenotypes have been demonstrated. Hp in patients with the Hp 1-1 phenotype is able to bind more hemoglobin on per gram basis than Hps containing products of the Hp 2 allele (Langlois M R and Delanghe J R (1996) Clin Chem 42: 1589–1600). Hp molecules in patients with the Hp 1-1 phenotype are also more efficient antioxidants, since the smaller size of Hp 1-1 facilitates its entry to extravascular sites of oxidative tissue injury compared to products of the Hp 2 allele. This also includes a significantly greater glomerular sieving of Hp in patients with Hp 1-1 (Bowman B H and Kurosky A. (1982) Adv Hum Gen 12: 189-26). Differences in protection against oxidative stress in patients with the different Hp phenotypes results in differing serum levels of other antioxidants such as vitamin C (Langlois M R et al., (1997) Am J Clin Nutr 66: 606–610).

Long-term microvascular and macrovascular complications cause major morbidity and mortality in patients with diabetes mellitus (DM) (Diabetes Control and Complications Trial Research Group. (1993) N Eng J Med 329: 977–986). Four such complications are diabetic retinopathy (DR), diabetic nephropathy (DN), myocardial infarction and markedly increased risk of restenosis after percutaneous transluminal coronary angioplasty (PTCA). Approximately one third of patients with DM will develop end stage renal disease necessitating renal replacement therapy, within 25 years of the onset of diabetes. Epidemiological studies have demonstrated the important contributions of age of onset, duration, type of DM, and adequacy of metabolic control to the development and severity of DN (Diabetes Control and Complications Trial Research Group. (1993) N Eng J Med 329: 977–986.; Reichard P et al, (1993) N Eng J Med 329: 304–309). Patients with DM also manifest a 50 % increase in the rate of restenosis after PTCA (Carrozza J P et al. (1993) Ann Int Med 118: 344–349) compared to non-diabetics with an incidence as high as 70 % in some studies. This is particularly problematic in view of the increased incidence and extent of coronary artery disease in this population, often necessitating simultaneous treatment of multiple lesions in the same patient.

While numerous clinical trials have demonstrated anatomic predictors of restenosis in the diabetic and general populations (lesion length, vessel diameter) (Popma J J and Topol E J (1990) Am J Med 88: 16N–24N) there is currently little clinical information available to the clinician to predict which patients with DM are at greater risk for restenosis (Lincoff A M and Topol E J. (1997) Interventional catheterization techniques. In: Braunwald E, ed. Heart disease. $5^{th}$ ed. Philadelphia: W B Saunders pp. 1372–1374).

DR is one of the four major causes of blindness in the US (Ferris F L. et al. (1999) N Engl J Med 341: 667–678). Epidemiological studies have demonstrated that the age of diabetes onset, the duration of the diabetes, and the adequacy of metabolic control influence the development and severity of DR. However, it is well recognized that not all patients with DM will develop DR and that not all patients with DR progress to sight-threatening proliferative DR.

Considerable evidence has demonstrated the importance of the generation of reactive oxygen species (oxidative stress) in the development of diabetic vascular complications (Low PA et al. (1997) Diabetes 46: S38–S42; Hotta N. (1997) Nagoya J Med Sc 60: 89–100; Khechai F. et al. (1997) Art Thromb Vasc Bio 17: 2885–2290; Vlassara H. et al. (1986) Clin Chem 32: B37–41; Dominguez C. et al. (1998) Diab Care 21: 1736–1742; Ceriello A. et al. (1996) Diab 45: 471–477; Guigliano D. et al.(1996) Diab Care 19: 257–267; Asayama K. et al. (1993) Free Rad Biol Med 15: 597–602; Pfeiffer A and Schatz H.(1995) Exp Clin End Diab 103: 7–14).

Persistent hyperglycemia results in glucose auto-oxidation, protein glycation products, increased prostanoid synthesis and protein kinase activation, all of which lead to the increased production of oxygen free radicals. Advanced glycation end product (AGE) (Makita Z., et al. (1991) N Eng J Med 325: 836–842) accumulation has been directly implicated in tissue damage associated with DN (Clements R S. et al. (1998) J Diab Comp 12: 28–33). AGE and related oxidation specific adducts, such as carboxymethylysine and malondialdehyde-lysine, have been demonstrated to accumulate in the mesangial matrix and nodular lesions of DN (Suzuki D. et al. (1999) J Am Soc Neph 10: 822–832; Suzuki D. and Miyata T. (1999) Int Med 38: 309–314; Horrie K. et al. (1997) J Clin Invest 100: 2995–3004). Levels of endogenous antioxidants such as vitamin C (Retsky K L. And Frei B. (1995) Biochim Biophys A 1257: 279–287) are decreased in patients with diabetic nephropathy, further augmenting the burden of oxidative stress (Hirsch I B. et al. (1998) J Diab Comp 12: 259–263). One potential mechanism of the benefit of AGE inhibitors on the development of DN (Lewis E J. et al. (1993) N Engl J Med 329: 1456–1462; Bain R. et al. (1992) J Am Soc Nephr 3: S97–103) may be their ability to reduce oxidative stress and the production and deposition of AGE in the diabetic kidney.

Multiple studies have demonstrated the importance of oxidative stress in restenosis after PTCA. Free hemoglobin released as a result of red blood cell fragmentation at the site of vascular injury (Jacob H S. (1994) J Lab Clin Med 123: 808–816) can act as a potent oxidizing agent. A change in the oxidation state of the vascular milieu at the site of balloon injury has been directly linked to apoptosis of medial smooth muscle cells (Pollman M J. et al. (1999) Circ Res; 84: 113–121), activation of cytomegalovirus (Speir E. et al. (1996) Circ Res 79: 1143–1152) and activation of transcription factors (Hofmann M A. et al. (1998) Diab Care 21: 1310–1316) such as NF-κB which mediate the inflammatory response to balloon injury. Antioxidant therapy has been demonstrated to have a beneficial effect on restenosis after PTCA (Rodes J. et al. (1998) Circulation 97: 429–436; Nunes G L. et al. (1995) Arterioscl Thromb Vasc Biol 15: 156–165; Schneider J E. et al. (1993) Circ 88: 628–637; Tardif J C. et al. (1997) New Engl J Med 337: 365–372).

Myocardial ischemia in diabetic patients is often more severe than in non diabetic patients due to the diffuse nature of the disease. In addition, diabetic patients have been shown to have fewer coronary artery collateral blood vessels that may serve to bypass coronary artery stenoses and serve as alternative conduits for blood flow. Currently there is no way to predict which patients are most likely to be affected by this problem. This is because collateral formation is highly variable between patients. This variability can only partially be explained by differences in the rate of the development of the coronary artery occlusive disease. Factors associated with a decreased collateral formation in animals and in man include diabetes, aging, hypercholesterolemia, hypertension and cigarette smoking. A genetic basis for collateral formation in the setting of coronary diseases has been described but remains controversial because no specific gene associated with collateral formation has been identified.

PCT WO98/37419 teaches a method and kit for determining a haptoglobin phenotype and specifically relates to applications involving human haptoglobin. Teachings of this patent focus on use of the haptoglobin 2-2 phenotype as an independent risk factor, specifically in relation to target organ damage in refractory essential hypertension, in relation to atherosclerosis (in the general population) and acute myocardial infarction and in relation to mortality from HIV infection. This patent does not teach the use of haptoglobin phenotype as a risk factor in vascular complications in DM. Because of the tendency of a haptoglobin 2-2 phenotype to make patients more prone to oxidative stress, it might be argued that use of a 2-2 phenotype as a negative predictor for vascular complications in DM is indirectly implied by this patent. However, teachings of this patent do not include the idea that haptoglobin 1-1 phenotype is a positive predictor for reduced tendency towards vascular complications in DM. Teachings of PCT WO98/37419 include use of a haptoglobin binding partner.

In other words, it is known that oxidative stress originating from Hp 2-1 or 2-2 phenotype leads to vascular complications in the general populations. It is also known that certain vascular complications are associated with oxidative stress associated with DM. It is, therefore plausible to assume the oxidative stress originating from either Hp 2-1 or 2-2 phenotype combined with that originating from DM will result in diabetes associated vascular complications. At present, it is, however, not known and cannot be predicted whether Hp1-1 phenotype mitigates the vascular complications in diabetic patients. This is the case, because DM and Hp1-1 phenotypes have opposing effects on the level of oxidative stress.

The binding partner according to PCT WO98/37419 may be any molecule with at least two locations by which it binds haptoglobin. The locations may be formed by a peptide, antibody, or a portion thereof, or by a lectin, a cell receptor, a molecular imprint or a bacterial antigen or a portion thereof. Teachings of this patent focus specifically on the use of the T4 antigen of *S. pyogenes*. All haptoglobins contain both alpha chains and beta chains. Beta chains are identical in all haptoglobins, while alpha chains differ between the two alleles of the haptoglobin gene. The alpha 2 chain of haptoglobin is the result of a mutation based on an unequal crossing over and includes 142 amino acids, in contrast to the 83 amino acids of the alpha 1 chain. Immunologically the alpha 1 and alpha 2 chains are similar, with the exception of a unique sequence of amino is acid residues in the alpha 2 chain (Ala-Val-Gly-Asp-Lys-Leu-Pro-Glu-Cys-Glu-Ala-Asp-Asp-Gly-Gln-Pro-Pro-Pro-Lys-Cys-Ile, SEQ ID NO:1). Any portion of this unique peptide sequence is therefore a suitable epitope for raising antibodies to differentiate between haptoglobins containing alpha 1 and alpha 2 chains as described in "Using Antibodies: A Laboratory Manual" (Ed Harlow and David Lane eds., Cold Spring Harbor Laboratory Press (1999)) which is fully incorporated herein by reference. Such antibodies might be monoclonal, polyclonal, or any portion thereof and may be enriched or purified by any one of a number of techniques known to those skilled in the art. In addition, the nucleotide sequence encoding this sequence can be readily employed to differentiate among Hp genotypes.

There is thus a widely recognized need for, and it would be highly advantageous to have a method to predict which specific DM patients have lower risk with respect to vascular complications. Such a method would allow medical practitioners to make best use of available resources while minimizing risk to each patient to the greatest possible extent.

SUMMARY OF THE INVENTION

According to one aspect of the present invention there is provided a method of determining a potential of a hyperglycemic patient to develop vascular complications in response to oxidative stress, the method comprising the step of determining a haptoglobin phenotype of the hyperglycemic patient and thereby determining the potential of the hyperglycemic patient to develop vascular complications in response to oxidative stress.

According to another aspect of the present invention there is provided a method of determining the importance of reducing oxidative stress in a specific hyperglycemic patient, the method comprising the step of determining a haptoglobin phenotype, thereby determining the importance of reducing the oxidative stress in the specific hyperglycemic patient.

According to further features in preferred embodiments of the invention described below, the vascular complication is selected from the group consisting of a microvascular complication and a macrovascular complication.

According to still further features in the described preferred embodiments the vascular complication is a macrovascular complication selected from the group consisting of diabetic nephropathy, myocardial infarction and coronary angioplasty associated restenosis.

According to still further features in the described preferred embodiments the vascular complication is diabetic retinopathy.

According to still further features in the described preferred embodiments the vascular complication is selected from the group consisting of fewer coronary artery collateral blood vessels and myocardial ischemia.

According to still further features in the described preferred embodiments the step of determining the haptoglobin phenotype is effected by determining a haptoglobin genotype of the hyperglycemic patient.

According to still further features in the described preferred embodiments the step of determining a haptoglobin phenotype is effected by a method selected from the group consisting of a signal amplification method, a direct detection method and detection of at least one sequence change.

According to still further features in the described preferred embodiments the signal amplification method amplifies a molecule selected from the group consisting of a DNA molecule and an RNA molecule.

According to still further features in the described preferred embodiments the signal amplification method is selected from the group consisting of PCR, LCR (LAR), Self-Sustained Synthetic Reaction (3SR/NASBA) and Q-Beta (Qβ) Replicase reaction.

According to still further features in the described preferred embodiments the direct detection method is selected from the group consisting of a cycling probe reaction (CPR) and a branched DNA analysis.

According to still further features in the described preferred embodiments the detection of at least one sequence change employs a method selected from the group consisting of restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis and Dideoxy fingerprinting (ddF).

According to still further features in the described preferred embodiments the step of determining said haptoglobin phenotype is effected by directly determining the haptoglobin phenotype of the hyperglycemic patient.

According to still further features in the described preferred embodiments the step of determining said haptoglobin phenotype is effected by an immunological detection method According to still further features in the described preferred embodiments the immunological detection method is selected from the group consisting of a radio-immunoassay (RIA), an enzyme linked immunosorbent assay (ELISA), a western blot, an immunohistochemical analysis, and fluorescence activated cell sorting (FACS).

The present invention successfully addresses the shortcomings of the presently known configurations by providing methods for assessing the risk of oxidative stress in specific hypoglycemic patients and for determining which hypoglycemic patients are most likely to benefit from antioxidant therapy.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
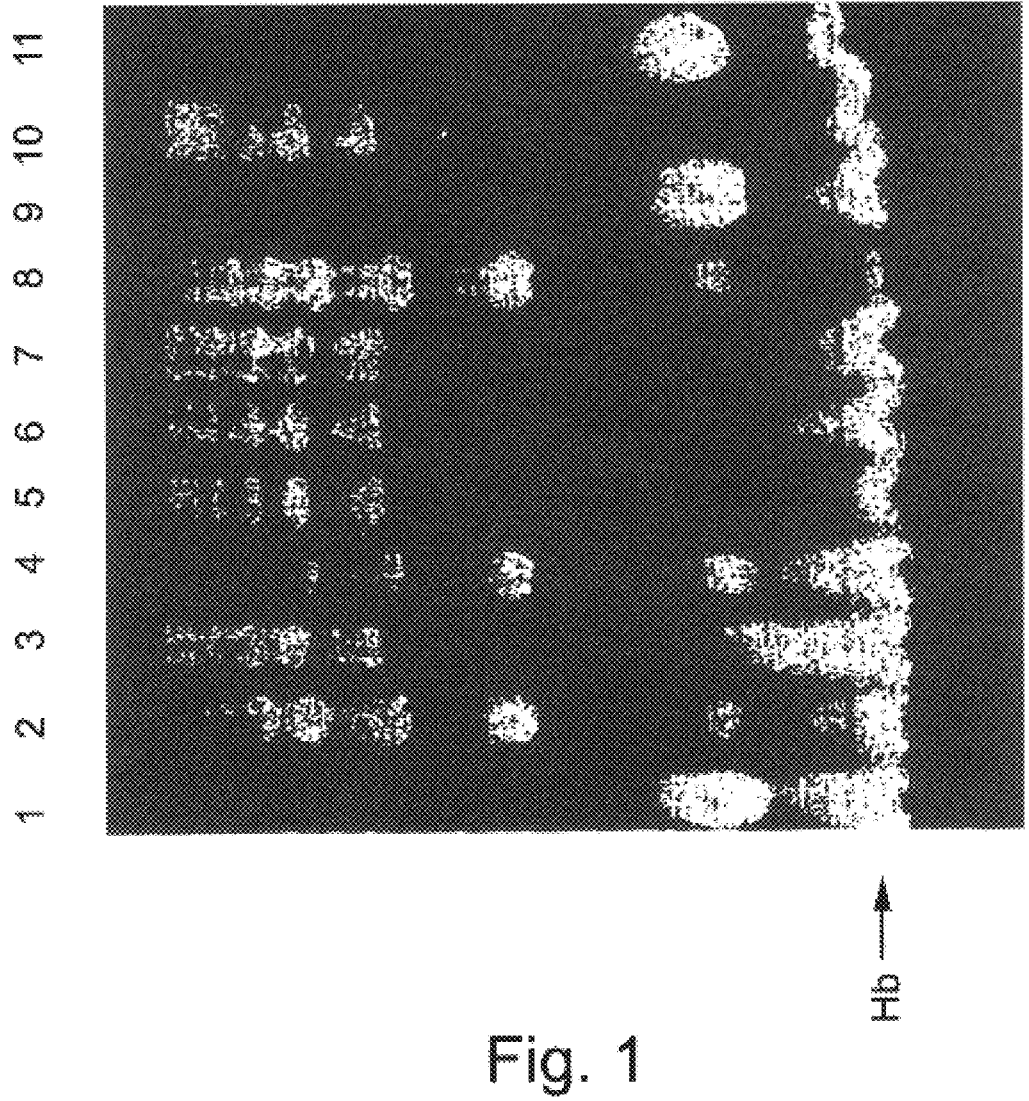
FIG. 1 shows representative electrophoretic patterns of Hp phenotypes 1-1, 2-1 and 2-2 as revealed by polyacrylamide gel electrophoresis of hemoglobin enriched serum. Hp 1-1 (lanes 1, 9 and 11) shows a single rapidly migrating protein band. Hp 2-2 (lanes 3, 5, 6, 7 and 10) has a series of slower migrating bands. Hp 2-1 (lanes 2, 4 and 8) displays another series of slowly migrating bands and a weak band that migrates similar to the Hp 1-1 band.

The present invention is of a method of determining the importance of reducing oxidative stress in a specific hyperglycemic patient and is further of a method of determining a potential of a hyperglycemic patient to develop vascular complications in response to oxidative stress. These methods can be used to determine appropriate treatment for hyperglycemic patients.

Specifically, the present invention can be used to evaluate the potential efficacy of anti-oxidant therapy as an adjunct to treatment for a hyperglycemic patient or to assess the risk of developing restenosis following cardiac catheterization in a hyperglycemic patient.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention is embodied by a method of determining a potential of a hyperglycemic patient to develop vascular complications in response to oxidative stress. The method includes the single step of determining a haptoglobin phenotype of the hyperglycemic patient and thereby determining the potential of the hyperglycemic patient to develop vascular complications in response to oxidative stress.

Figure 2:
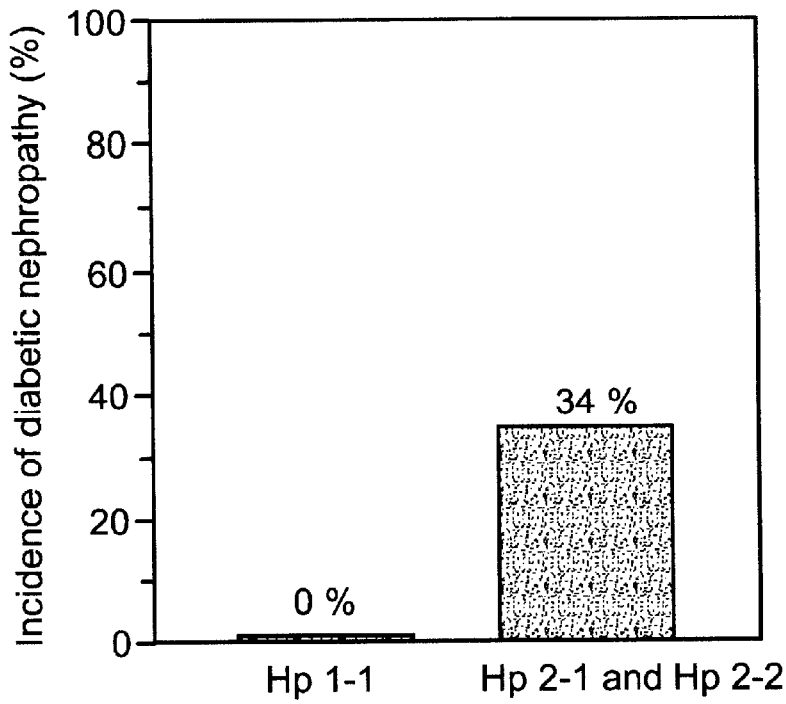
FIG. 2 is a frequency histogram of the incidence of diabetic nephropathy in type I DM patients with different Hp phenotypes. There were 13 patients with Hp 1-1 and 41 patients with Hp 2-1 or 2-2. None of the patients with Hp 1-1 developed DN and 14 of the Hp 2-1 or 2-2 patients developed DN (0% vs. 34%, p<0.02)
Figure 3:
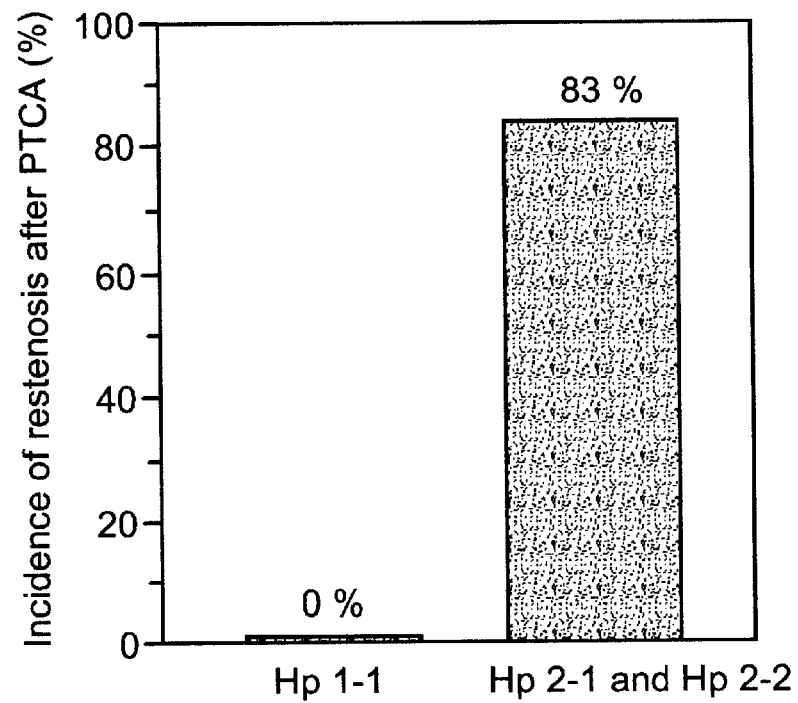
FIG. 3 is a frequency histogram of the incidence of restenosis (greater than 50% narrowing of lumen) after PTCA in type II DM patients with different Hp phenotypes. There were 5 patients with Hp 1-1 and 40 patients with Hp 2-1 or 2-2. None of the patients with Hp 1-1 developed restenosis after PTCA where as 33 patients with the Hp 2-1 or 2-2 phenotype developed restenosis (0% vs. 83%, p<0.0006).

The utility of this method is demonstrated by data presented in Tables 1, 2, and 3 as well as by FIGS. 2 and 3 hereinbelow. One method of determining a haptoglobin phenotype, Polyacrylamide gel electrophoresis, is demonstrated by FIG. 1.

The present invention is further embodied by a method of determining the importance of reducing oxidative stress in a specific hyperglycemic patient. The method includes the single step of determining a haptoglobin phenotype, thereby determining the importance of reducing the oxidative stress in the specific hyperglycemic patient.

Since the haptoglobin 1-1 genotype reduces oxidative stress, and since the haptoglobin 1-1 phenotype has a sparing effect with respect to several vascular complications associated with chronic hyperglycemia as detailed hereinbelow and as demonstrated by data summarized in Tables 1, 2, and 3 and by FIGS. 2 and 3, it can be inferred that other methods for reducing oxidative stress are advisable for chronically hyperglycemic patients with haptoglobin 2-1 or 2-2 phenotypes.

Anti-oxidant therapy using the drug probucol with and without multivitamins has been demonstrated to reduce the incidence of restenosis after PTCA in the general population. However, its use is not widespread due to the need to begin therapy at least 4 weeks prior to the PTCA. The long treatment protocol makes many patients reticent to undergo the treatment. Use of the method of the present invention is expected to help those patients at highest risk understand the importance of an anti-oxidative therapy regimen there are other antioxidative therapies available and I presume these would be covered.

The vascular complication referred to hereinabove may be either a microvascular complication or a macrovascular complication. Examples of macrovascular complications include, but are not limited to, diabetic nephropathy, myocardial infarction and coronary angioplasty associated restenosis. Alternately or additionally, the vascular complication may be diabetic retinopathy, which is a microvascular complication. Other complications include fewer coronary artery collateral blood vessels and myocardial ischemia.

According to various preferred embodiments of the present invention, the step of determining a haptoglobin phenotype is effected any one of a variety of methods including, but not limited to, a signal amplification method, a direct detection method and detection of at least one sequence change. These methods determine a phenotype indirectly, by determining a genotype. As will be explained hereinbelow, determination of a haptoglobin phenotype may also be accomplished directly by analysis of haptoglobin gene products.

The signal amplification method according to various preferred embodiments of the present invention may amplify, for example, a DNA molecule or an RNA molecule. Signal amplification methods which might be used as part of the present invention include, but are not limited to PCR, LCR (LAR), Self-Sustained Synthetic Reaction (3SR/NASBA) or a Q-Beta (Qβ) Replicase reaction.

Polymerase Chain Reaction (PCR): The polymerase chain reaction (PCR), as described in U.S. Pat. No. 4,683,195 and U.S. Pat. No. 4,683,202 to Mullis and Mullis et al., is a method of increasing the concentration of a segment of target sequence in a mixture of genomic DNA without cloning or purification. This technology provides one approach to the problems of low target sequence concentration. PCR can be used to directly increase the concentration of the target to an easily detectable level. This process for amplifying the target sequence involves the introduction of a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization (annealing), and polymerase extension (elongation) can be repeated as often as needed, in order to obtain relatively high concentrations of a segment of the desired target sequence.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

Ligase Chain Reaction (LCR or LAR): The ligase chain reaction [LCR; sometimes referred to as "Ligase Amplification Reaction" (LAR)] described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method of amplifying nucleic acids. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, and ligation amplify a short segment of DNA. LCR has also been used in combination with PCR to achieve enhanced detection of single-base changes. Segev, PCT Publication No. W09001069 A1 (1990). However, because the four oligonucleotides used in this assay can pair to form two short ligateable fragments, there is the potential for the generation of target-independent background signal. The use of LCR for mutant screening is limited to the examination of specific nucleic acid positions.

Self-Sustained Synthetic Reaction (3SR/NASBA): The self-sustained sequence replication reaction (3SR) (Guatelli et al., Proc. Natl. Acad. Sci., 87:1874–1878, 1990), with an erratum at Proc. Natl. Acad. Sci., 87:7797, 1990) is a transcription-based in vitro amplification system (Kwok et al., Proc. Natl. Acad. Sci., 86:1173–1177, 1989) that can exponentially amplify RNA sequences at a uniform temperature. The amplified RNA can then be utilized for mutation detection (Fahy et al., PCR Meth. Appl., 1:25–33, 1991). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo-and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200–300 base pairs).

Q-Beta (Qβ) Replicase: In this method, a probe which recognizes the sequence of interest is attached to the replicatable RNA template for Qβ replicase. A previously identified major problem with false positives resulting from the replication of unhybridized probes has been addressed through use of a sequence-specific ligation step. However, available thermostable DNA ligases are not effective on this RNA substrate, so the ligation must be performed by T4 DNA ligase at low temperatures (37 degrees C.). This prevents the use of high temperature as a means of achieving specificity as in the LCR, the ligation event can be used to detect a mutation at the junction site, but not elsewhere.

A successful diagnostic method must be very specific. A straight-forward method of controlling the specificity of nucleic acid hybridization is by controlling the temperature of the reaction. While the 3SR/NASBA, and Qβ systems are all able to generate a large quantity of signal, one or more of the enzymes involved in each cannot be used at to high temperature (i.e., >55 degrees C.). Therefore the reaction temperatures cannot be raised to prevent non-specific hybridization of the probes. If probes are shortened in order to make them melt more easily at low temperatures, the likelihood of having more than one perfect match in a complex genome increases. For these reasons, PCR and LCR currently dominate the research field in detection technologies.

The basis of the amplification procedure in the PCR and LCR is the fact that the products of one cycle become usable templates in all subsequent cycles, consequently doubling the population with each cycle.

The final yield of any such doubling system can be expressed as: $(1+X)^n = y$, where "X" is the mean efficiency (percent copied in each cycle), "n" is the number of cycles, and "y" is the overall efficiency, or yield of the reaction (Mullis, PCR Methods Applic., 1:1, 1991). If every copy of a target DNA is utilized as a template in every cycle of a polymerase chain reaction, then the mean efficiency is 100 %. If 20 cycles of PCR are performed, then the yield will be $2^{20}$, or 1,048,576 copies of the starting material. If the reaction conditions reduce the mean efficiency to 85 %, then the yield in those 20 cycles will be only $1.85^{20}$, or 220,513 copies of the starting material. In other words, a PCR running at 85 % efficiency will yield only 21 % as much final product, compared to a reaction running at 100 % efficiency. A reaction that is reduced to 50 % mean efficiency will yield less than 1 % of the possible product.

In practice, routine polymerase chain reactions rarely achieve the theoretical maximum yield, and PCRs are usually run for more than 20 cycles to compensate for the lower yield. At 50 % mean efficiency, it would take 34 cycles to achieve the million-fold amplification theoretically possible in 20, and at lower efficiencies, the number of cycles required becomes prohibitive. In addition, any background products that amplify with a better mean efficiency than the intended target will become the dominant products.

Also, many variables can influence the mean efficiency of PCR, including target DNA length and secondary structure, primer length and design, primer and dNTP concentrations, and buffer composition, to name but a few. Contamination of the reaction with exogenous DNA (e.g., DNA spilled onto lab surfaces) or cross-contamination is also a major consideration. Reaction conditions must be carefully optimized for each different primer pair and target sequence, and the process can take days, even for an experienced investigator. The laboriousness of this process, including numerous technical considerations and other factors, presents a significant drawback to using PCR in the clinical setting. Indeed, PCR has yet to penetrate the clinical market in a significant way. The same concerns arise with LCR, as LCR must also be optimized to use different oligonucleotide sequences for each target sequence. In addition, both methods require expensive equipment, capable of precise temperature cycling.

Many applications of nucleic acid detection technologies, such as in studies of allelic variation, involve not only detection of a specific sequence in a complex background, but also the discrimination between sequences with few, or single, nucleotide differences. One method of the detection of allele-specific variants by PCR is based upon the fact that it is difficult for Taq polymerase to synthesize a DNA strand when there is mismatch between the template strand and the 3' end of the primer. An allele-specific variant may be detected by the use of a primer that is perfectly matched with only one of the possible alleles; the mismatch to the other allele acts to prevent the extension of the primer, thereby preventing the amplification of that sequence. This method has a substantial limitation in that the base composition of the mismatch influences the ability to prevent extension across the mismatch, and certain mismatches do not prevent extension or have only a minimal effect (Kwok et al., Nucl. Acids Res., 18:999, 1990)

A similar 3'-mismatch strategy is used with greater effect to prevent ligation in the LCR (Barany, PCR Meth. Applic., 1:5, 1991). Any mismatch effectively blocks the action of the thermostable ligase, but LCR still has the drawback of target-independent background ligation products initiating the amplification. Moreover, the combination of PCR with subsequent LCR to identify the nucleotides at individual positions is also a clearly cumbersome proposition for the clinical laboratory.

The direct detection method according to various preferred embodiments of the present invention may be, for example a cycling probe reaction (CPR) or a branched DNA analysis.

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern band RNase protection assays usually require the use of radioactivity and are not amenable to automation. Recently devised techniques have sought to eliminate the use of radioactivity and/or improve the sensitivity in automateable formats. Two examples are the "Cycling Probe Reaction" (CPR), and "Branched DNA" (bDNA).

Cycling probe reaction (CPR): The cycling probe reaction (CPR) (Duck et al., BioTech., 9:142, 1990), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Branched DNA: Branched DNA (bDNA), described by Urdea et al., Gene 61:253–264 (1987), involves oligonucleotides with branched structures that allow each individual oligonucleotide to carry 35 to 40 labels (e.g., alkaline phosphatase enzymes). While this enhances the signal from a hybridization event, signal from non-specific binding is similarly increased.

The detection of at least one sequence change according to various referred embodiments of the present invention may be accomplished by, for example restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis or Dideoxy fingerprinting (ddF).

The demand for tests which allow the detection of specific nucleic acid sequences and sequence changes is growing rapidly in clinical diagnostics. As nucleic acid sequence data for genes from humans and pathogenic organisms accumulates, the demand for fast, cost-effective, and easy-to-use tests for as yet mutations within specific sequences is rapidly increasing.

A handful of methods have been devised to scan nucleic acid segments for mutations. One option is to determine the entire gene sequence of each test sample (e.g., a bacterial isolate). For sequences under approximately 600 nucleotides, this may be accomplished using amplified material (e.g., PCR reaction products). This avoids the time and expense associated with cloning the segment of interest. However, specialized equipment and highly trained personnel are required, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Restriction fragment length polymorphism (RFLP): For detection of single-base differences between like sequences, the requirements of the analysis are often at the highest level of resolution. For cases in which the position of the nucleotide in question is known in advance, several methods have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis).

Single point mutations have been also detected by the creation or destruction of RFLPs. Mutations are detected and localized by the presence and size of the RNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807–6817, 1990). However, this method requires the use of osmium tetroxide and piperidine, two highly noxious chemicals which are not suited for use in a clinical laboratory.

RFLP analysis suffers from low sensitivity and requires a large amount of sample. When RFLP analysis is used for the detection of point mutations, it is, by its nature, limited to the detection of only those single base changes which fall within a restriction sequence of a known restriction endonuclease. Moreover, the majority of the available enzymes have 4 to 6 base-pair recognition sequences, and cleave too frequently for many large-scale DNA manipulations (Eckstein and Lilley (eds.), Nucleic Acids and Molecular Biology, vol. 2, Springer-Verlag, Heidelberg, 1988). Thus, it is applicable only in a small fraction of cases, as most mutations do not fall within such sites.

A handful of rare-cutting restriction enzymes with 8 base-pair specificities have been isolated and these are widely used in genetic napping, but these enzymes are few in number, are limited to the recognition of G+C-rich sequences, and cleave at sites that tend to be highly clustered (Barlow and Lehrach, Trends Genet., 3:167, 1987). Recently, endonucleases encoded by group I introns have been discovered that might have greater than 12 base-pair specificity (Perlman and Butow, Science 246:1106, 1989), but again, these are few in number.

Allele specific oligonucleotide (ASO): If the change is not in a recognition sequence, then allele-specific oligonucleotides (ASOs), can be designed to hybridize in proximity to the mutated nucleotide, such that a primer extension or ligation event can bused as the indicator of a match or a mis-match. Hybridization with radioactively labeled allelic specific oligonucleotides (ASO) also has been applied to the detection of specific point mutations (Conner et al., Proc. Natl. Acad. Sci., 80:278–282, 1983). The method is based on the differences in the melting temperature of short DNA fragments differing by a single nucleotide. Stringent hybridization and washing conditions can differentiate between mutant and wild-type alleles. The ASO approach applied to PCR products also has been extensively utilized by various researchers to detect and characterize point mutations in ras genes (Vogelstein et al., N. Eng. J. Med., 319:525–532, 1988; and Farr et al., Proc. Natl. Acad. Sci., 85:1629–1633, 1988), and gsp/gip oncogenes (Lyons et al., Science 249:655–659, 1990). Because of the presence of various nucleotide changes in multiple positions, the ASO method requires the use of many oligonucleotides to cover all possible oncogenic mutations.

With either of the techniques described above (i.e., RFLP and ASO), the precise location of the suspected mutation must be known in advance of the test. That is to say, they are inapplicable when one needs to detect the presence of a mutation within a gene or sequence of interest.

Denaturing/Temperature Gradient Gel Electrophoresis DGGE/TGGE): Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of mutations in the target sequences because of the corresponding changes in their electrophoretic mobilities. The fragments to be analyzed, usually PCR products, are "clamped" at one end by a long stretch of G-C base pairs (30–80) to allow complete denaturation of the sequence of interest without complete dissociation of the strands. The attachment of a GC "clamp" to the DNA fragments increases the fraction of mutations that can be recognized by DGGE (Abrams et al., Genomics 7:463–475, 1990). Attaching a GC clamp to one primer is critical to ensure that the amplified sequence has a low dissociation temperature (Sheffield et al., Proc. Natl. Acad. Sci., 86:232–236, 1989; and Lerman and Silverstein, Meth. Enzymol., 155:482–501, 1987). Modifications of the technique have been developed, using temperature gradients (Wartell et al., Nucl. Acids Res., 18:2699–2701, 1990), and the method can be also applied to RNA:RNA duplexes (Smith et al., Genomics 3:217–223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405, 1991). CDGE requires that gels be performed under different denaturant conditions in order to reach high efficiency for the detection of mutations.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Single-Strand Conformation Polymorphism (SSCP): Another common method, called "Single-Strand Conformation Polymorphism" (SSCP) was developed by Hayashi, Sekya and colleagues (reviewed by Hayashi, PCR Meth. Appl., 1:34–38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874–879, 1989).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy fingerprinting (ddF): The dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200–300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion subcloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

According to a presently preferred embodiment of the present invention the step of searching for the mutation or mutations in any of the genes listed above, such as, for example, the reduced folate carrier (RFC) gene, in tumor cells or in cells derived from a cancer patient is effected by a single strand conformational polymorphism (SSCP) technique, such as cDNA-SSCP or genomic DNA-SSCP. However, alternative methods can be employed, including, but not limited to, nucleic acid sequencing, polymerase chain reaction, ligase chain reaction, self-sustained synthetic reaction, Qβ-Replicase, cycling probe reaction, branched DNA, restriction fragment length polymorphism analysis, mismatch chemical cleavage, heteroduplex analysis, allele-specific oligonucleotides, denaturing gradient gel electrophoresis, constant denaturant gel electrophoresis, temperature gradient gel electrophoresis and dideoxy fingerprinting.

Determination of a haptoglobin phenotype may, as if further exemplified in the Examples section that follows, also be accomplished directly, by analyzing the protein gene products of the haptoglobin gene, or portions thereof. Such a direct analysis is often accomplished using an immunological detection method.

Immunological detection methods are fully explained in, for example, "Using Antibodies: A Laboratory Manual" (Ed Harlow, David Lane eds., Cold Spring Harbor Laboratory Press (1999)) and those familiar with the art will be capable of implementing the various techniques summarized hereinbelow as part of the present invention. All of the immunological techniques require antibodies specific to at least one of the two haptoglobin alleles. Immunological detection methods suited for use as part of the present invention include, but are not limited to, radio-immunoassay (RIA), enzyme linked immunosorbent assay (ELISA), western blot, immunohistochemical analysis, and fluorescence activated cell sorting (FACS).

Radio-immunoassay (RIA): In one version, this method involves precipitation of the desired substrate, haptoglobin in this case and in the methods detailed hereinbelow, with a specific antibody and radiolabelled antibody binding protein (e.g., protein A labeled with $I^{125}$) immobilized on a precipitable carrier such as agarose beads. The number of counts in the precipitated pellet is proportional to the amount of substrate.

In an alternate version of the RIA, A labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a calorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a calorimetric reaction may be required.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

It will be appreciated by one ordinarily skilled in the art that determining the haptoglobin phenotype of an individual, either directly or genetically, may be effected using any suitable biological sample derived from the examined individual, including, but not limited to, blood, plasma, blood cells, saliva or cells derived by mouth wash, and body secretions such as urine and tears, etc.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. No. 4,666,828; U.S. Pat. No. 4,683,202; U.S. Pat. No. 4,801,531; U.S. Pat. No. 5,192,659 and U.S. Pat. No. 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. No. 3,791,932; U.S. Pat. No. 3,839,153; U.S. Pat. No. 3,850,752; U.S. Pat. No. 3,850,578; U.S. Pat. No. 3,853,987; U.S. Pat. No. 3,867,517; U.S. Pat. No. 3,879,262; U.S. Pat. No. 3,901,654; U.S. Pat. No. 3,935,074; U.S. Pat. No. 3,984,533; U.S. Pat. No. 3,996,345; U.S. Pat. No. 4,034,074; U.S. Pat. No. 4,098,876; U.S. Pat. No. 4,879,219, U.S. Pat. No. 5,011,771 and U.S. Pat. No. 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXPERIMENTAL METHODS

Before presenting examples which provide experimental data to support the present invention, reference is made to the following methods:

Patients: All protocols were approved by Human Research Ethics Committee of the Rambam Medical Center. Informed consent was obtained from all patients. All patients were recruited from the Rambam Medical Center in Haifa, Israel Haptoglobin phenotyping: Haptoglobin phenotyping was determined from 10 µl of hemoglobin-enriched serum by gel electrophoresis and peroxidase staining, using a modification of the method originally described by Smithies which used starch gel electrophoresis and peroxidase staining with benzidine (Linke R P. (1984) Anal Biochem 141: 55–61; Wassell J. and Keevil B (1999) Ann Clin Biochem 36: 609–612; Smithies O. (1955) Biochem 61: 629–641). All chemical reagents were supplied by Sigma (Rehovot, Israel).

Briefly, 2 μl of a 10% hemoglobin solution in water was added to 10 μl of serum and the samples allowed to stand for 5 minutes at room temperature in order to allow the Hp-Hb complexes to form. An equal volume of sample buffer containing 20% glycerol, 125 mm TrisHCl pH 6.8 and 0.001% bromophenol blue was added to each sample prior to running on the gel. The Hb-Hp complex was resolved by polyacrylamide gel electrophoresis using a buffer containing 25 mM TrisHCl and 192 mM glycine. The stacking gel was 4% polyacrylamide (29:1 acrylamide/bis acrylamide) in 125 mM TrisHCl, pH 6.8 and the separating gel was 4.7 % polyacrylamide (29:1 acrylamide/bis acrylamide) in 360 mM TrisHCl, pH 8.8. Electrophoresis was performed at a constant voltage of 300V for 3 hours. After the electrophoresis was completed the Hp-Hb complexes were visualized by soaking the gel in freshly prepared staining solution in a glass tray. The staining solution (prepared by adding the reagents in the order listed) contained 5 ml of 0.2 % (w/v) 3,3', 5,5,'-tetramethylbenzidine in methanol, 0.5 ml of dimethylsulfoxide, 10 ml of glacial acetic acid, 1 ml of 1 % (w/v) potassium ferricyanide and 150 μl of 30% (w/w) hydrogen peroxide. The bands corresponding to the Hp-Hb complex were readily visible within 15 minutes and were stable for over 48 hours. All gels were documented with photographs. The haptoglobin phenotype of the sample was determined from the gel in a masked fashion without any knowledge of DR, urinary albumin excretion rate or the presence of restenosis after PTCA. A representative gel demonstrating the ease and lack of ambiguity in identifying the different phenotypes is shown in FIG. 1.

Collateral Coronary Artery Analysis: The number of diseased epicardial vessels, ranging from one to three, was determined based on the number of major epicardial vessels found to have at least one 70% stenosis. On a separate sheet the patient's coronary collateral score (yes or no collaterals) was recorded by an experienced angiographer. The collateral scoring system used was modified from the TIMI system (Habib G, et al. (1991) Circulation 83: 739–746), based on the presence or absence of collateral vessels and opacification of the recipient vessel. For all patients the collateral score was determined and documented prior to Hp phenotyping. Statistical analysis: For the study of the relationship of Hp phenotype to DN a Chi square test was employed to compare the incidence of no nephropathy, microalbuminuria and microalbuminuria between patients with the 1-1 haptoglobin phenotype and the pooled Hp 2-1 and 2-2 phenotypes. The same test was used to determine whether these two groups (Hp 1-1 vs. Hp other) differed in age, sex, age of onset of DM, duration of DM, or HbA1c. Fisher exact p values were employed for categorical variables and the Wilcoxon 2 independent sample test was used for continuous variables. All p values are based on a two-tailed comparison.

For the study of the relationship of Hp phenotype to restenosis in patients with DM a Chi square test was employed to compare the incidence of stenosis (greater than 50%) between patients with the 1-1 haptoglobin phenotype and those with either Hp 2-1 or 2-2 phenotypes. A Chi square test was also used to determine whether these two groups (Hp 1-1 vs. Hp other) differed in age, sex, time since PTCA, length of lesion, diameter of lesion, presence of stent, hypertension, elevated lipids, smoking, and medications. Fisher exact p values were used for categorical variables and the Wilcoxon 2 independent sample test was used for the continuous variables length of lesion, diameter of lesion and time since PTCA since these variables were not normally distributed. Age and % stenosis were analyzed by independent t tests. % stenosis was determined using the following scoring system: 1=0% stenosis; 2=10% stenosis; 3=10–25% stenosis; 4=25–50% stenosis; 5 =50–75% stenosis; 6=75–90% stenosis; 7=>90% stenosis; 8=>99% stenosis and 9=100% stenosis. Allele frequencies for the Hp alleles were consistent with those previously reported for populations in this region, and were in Hardy Weinberg equilibrium (Nevo S. and Tatarsky I. (1986) Human Gen 73: 240–244). For the study of the relationship of Hp phenotype to coronary collateral formation the Chi square test was used.

EXPERIMENTAL RESULTS

Haptoglobin and Diabetic Retinopathy (DR): In order to determine the relationship of Hp phenotype and DR, 52 consecutive type I DM patients over a 3-month period were recruited from an outpatient diabetes clinic. All patients were documented to have Type I DM of at least 10 years duration. Hp phenotype was determined from 10 μl of hemoglobin-enriched serum as described hereinabove. DR was determined using seven-field stereoscopic fundal photography performed and read by an experienced reader using standardized criteria. Determination of the presence or absence of DR was conducted without any knowledge of the Hp phenotype. Absence of DR was defined as complete absence of macular edema, hard exudates, blot hemorrhages, microaneurysms, venous beading, intraretinal microvascular abnormalities, cotton wool spots or neovascularization. Proliferative retinopathy was said to be present if neovascularization was evident. It transpired that 48% (n=25) of the study population had evidence of DR and 19% (n=10) had proliferative DR (Table 1). The distribution of the three Hp phenotypes was 12 (1-1), 20 (2-1) and 20 (2-2). There was a significantly lower incidence of DR in patients with the 1-1 as compared to the 2-1 and 2-2 phenotypes ($^{1}/_{12}$ vs. $^{24}/_{40}$, p<0.002). delete, this is not statistically significant There was no significant difference in the age, sex, hemoglobin $A_1c$, age of onset of diabetes, or duration of diabetes between patients with and without the Hp 1-1 phenotype.

These data demonstrate that patients with the Hp 1-1 phenotype are provided increased protection against DR. This protection provided by Hp 1-1 is apparently due to its superior anti-oxidative and hemoglobin-binding capacity compared to Hp 2-1 and 2-2. These findings suggest that vigorous antioxidant therapy may prevent the development of DR in those DM type I patients expressing the Hp 2 allele.

TABLE 1

Haptoglobin and Diabetic Retinopathy

|  | Hp 1-1 | Hp 2-1 and 2-2 | P |
| --- | --- | --- | --- |
| Number of patients | 12 | 40 |  |
| Age | 31 +/− 15.1 | 38.6 +/− 15.0 | NS |
| Sex (% male) | 75 | 52.5 | NS |
| Age of onset of diabetes | 14.4 +/− 10.8 | 19.0 +/− 11.6 | NS |
| Duration of diabetes | 17.3 +/− 7.7 | 19.9 +/− 10.2 | NS |
| Hemoglobin A1c | 7.4 +/− 1.0 | 8.0 +/− 1.5 | NS |
| Incidence of DR (%) | 8.3 | 60.0 | 0.002 |

Categorical variables were compared using Chi square test with Fisher exact p values and continuous variables by Wilcoxon 2 independent sample test. Values are given as the mean +/− SD.

Haptoglobin phenotype and Diabetic Nephropathy: Inclusion criteria for the diabetic retinopathy study were documented Type 1 DM for at least 10 years, no hypertension, and serum creatinine less than 170 μmol/L. Fifty three consecutive patients from an outpatient diabetes clinic who met these inclusion criteria were included in the study. For all patients a 3–5 hour timed urine collection was obtained in the clinic for the determination of UAE. Patients with a UAE of <30 mg/day were classified as not having DN. Microalbuminuria was defined as an UAE of 30–300 mg per 24 hours. The only exception were patients with greater than 30 years of type 1 DM, without overt proteinuria (UAE<300 mg/day), who were classified as not having DN (Warram J H. et al. (1996) J Am Soc Neph 7: 930–937). Determination of the urinary excretion of albumin was conducted in a masked fashion, without any knowledge of the haptoglobin phenotype. There was no significant difference in the age, sex, and age of onset or duration of diabetes between the patients with the 1-1 phenotype and other phenotypes (Table 2).

TABLE 2

Characteristics of Patients in Diabetic Nephropathy Study According to Hp Phenotype

| Variable | HP 1-1 | Hp 2-1 or 2-2 | $X^2/Z$ | P |
|---|---|---|---|---|
| n | 12 | 41 | | |
| male (%) | 75 | 53.7 | 1.74 | NS |
| Age (+/− SD) | 31.5 +/− 15.1 | 36.4 +/− 14.8 | −1.00 | NS |
| Age onset DM (+/− SD) | 14.4 +/− 10.8 | 18.2 +/− 11.7 | −0.80 | NS |
| Duration of DM (+/− SD) | 17.3 +/− 7.7 | 18.4 +/− 8.7 | −0.63 | NS |
| Hemoglobin $A_1c$(+/− SD) | 7.4 +/− 1.0 | 8.1 +/− 1.7 | −1.00 | NS |

Of the patients with type 1 DM of at least 10 years duration, only 14 patients demonstrated microalbuminuria as defined hereinabove. Five of these 14 patients demonstrated macroalbuminuria as defined hereinabove. The remaining 39 patients did not fulfill criteria for DN as outlined hereinabove.

Significantly, none of the 13 patients with the Hp 1-1 phenotype had DN. As shown in FIG. 2, there was a highly significant difference in the incident of DN between patients with the Hp 1-1 phenotype and the other phenotypes (0% vs. 34%, p<0.02).

These results suggest that vigorous antioxidant therapy may ameliorate diabetic complications in the subset of patients whose Hp phenotype suggests that they are at greater risk. ACE (angiotensin converting enzyme inhibitor) inhibitor therapy has been demonstrated to have a beneficial effect on the development and progression of DN that cannot be attributed entirely to its affect on arterial blood pressure (results of the HOPE study and MICRO-HOPE substudy (2000) Lancet 355:253–259). Although intraglomulerular hemodynamic effects may explain in large measure the renoprotective effect of this class of agents, some studies have also suggested a role for the anti-oxidant effect of these agents. In particular, ACE inhibitors result in a reduction of heme driven oxidation products accumulating in the kidney and at least part of their beneficial action may be mediated by their role as antioxidants. Such beneficial effects may become more evident as study groups are stratified by Hp phenotype according to risk for oxidant mediated vascular injury.

Haptoglobin Phenotype and Restenosis after Coronary Angioplasty: Patients were recruited from those presenting for diagnostic evaluation of coronary artery ischemia to the coronary catheterization laboratory. Inclusion criteria for the study were: documented type II DM and angioplasty done more than 4 months prior to the current catheterization at the Rambam Medical Center. Forty-five consecutive patients who met these inclusion criteria were included in this study. The site of the prior PTCA was characterized according to the length of the lesion, the diameter of lesion and whether a stent was implanted. Restenosis was said to be present if their was a greater than 50 % reduction of luminal diameter. Determination of the presence or absence of restenosis was done in a masked fashion without any knowledge of the haptoglobin phenotype. There was no significant difference in the age, sex, time since PTCA, length of lesion, diameter of lesion, presence of stent, hypertension, elevated lipids, smoking, and medications between the patients with the 1 -1 phenotype versus the other phenotypes (Table 3).

TABLE 3

Characteristics of Patients in Restenosis Study According to Hp Phenotype

| Variable | Hp 1-1 | Hp 2-1 or 2-2 | $X^2/Z$ | P |
|---|---|---|---|---|
| N | 5 | 40 | | |
| Male (%) | 80.0 | 75 | | NS |
| Hypertension (%) | 60.0 | 62.5 | | NS |
| PTCA interval (+/− SD) | 29.8 +/− 23.6 | 21.9 +/− 24.6 | | NS |
| Lesion diameter (+/− SD) | 3.2 +/− 0.6 | 3.0 +/− 0.5 | | NS |
| Lesion length (+/− SD) | 17.6 +/− 11.7 | 14.3 +/− 7.2 | | NS |
| % stenosis (+/− SD) | 1.8 +/− 1.1 | 4.6 +/− 2.1 | | NS |
| ACE inhibitor (%) | 60.0 | 75 | | NS |
| Age (+/− SD) | 62 +/− 10.9 | 59.3 +/− 0.65 | | NS |

The overall incidence of restenosis in the 45 patients in the study was 73%. None of the 5 patients with the 1-1 Hp phenotype demonstrated restenosis. In contrast, 83 % ($^{33}/_{40}$) of the patients with Hp 2-1 or 2-2 demonstrated restenosis. The difference in the rate of restenosis between patients with the different Hp phenotypes was highly significant (FIG. 3).

These results suggest that vigorous antioxidant therapy may ameliorate diabetic complications in the subset of patients whose Hp phenotype suggests that they are at greater risk. Anti-oxidant therapy using a drug, probucol, with or without multivitamins has been demonstrated to reduce the incidence of restenosis after PTCA (Tardif J C. et al. (1997) New Engl J Med 337: 365–372.), but its use is not widespread probably because of the apparent need to begin therapy at least 4 weeks prior to the PTCA. However, such a regimen might be especially beneficial to patients with the Hp 2-1 or 2-2 phenotype. Other antioxidant regimes may also be practiced.

Haptoglobin phenotype and coronary artery collateral blood vessels: Coronary artery collateral blood vessels were assessed using standard TIMI (thrombolysis in myocardial infarction trial) criteria in 186 consecutive patients. Hp phenotyping was performed by polyacrylamide gel electrophoresis of hemoglobin enriched serum with peroxidase staining as described hereinabove. Patients with Hp 1-1 and 2-1 were significantly more likely to have coronary artery collateral blood vessels than patients with Hp 2-2 (65% vs 44%, p<O.02). Moreover in the 46 diabetic patients included in the study this finding was more pronounced (84% of diabetic patients with Hp 1-1 or 2-1 had collaterals compared to 44% of diabetic patients with Hp 2-2, p<O.02). This suggests that patients, especially htperglycemic patients, with at least one haptoglobin 1 allele are less likely to suffer from a macrovascular complication in the form of a myocardial infarction. No other assayed parameters separated the patients into statisitically significant groups (Table 4) nor were haptoglobin phenotypes correlated with any other parameters (Table 5). These data demonstrate that Hp phenotype predicts in all patients, but in diabetic patients with increased specificity and power, the ability to grow collateral coronary arteries. Specifically patients with the Hp 1-1 or Hp 2-1 phenotype grow collaterals more efficiently than patients with the Hp 2-2 phenotype. This is consistent with previous reports showing that patients with the Hp 2-2 phenotype have larger myocardial infarctions. In other words, patients with the HP-2-2 phenotype are at increased risk of a macrovascular complication in the form of a myocardial infarction.

TABLE 4

Characteristics of Patients with and without Collateral Coronary Arteries

| | Collaterals | | |
|---|---|---|---|
| | no | yes | p |
| n | 85 | 102 | |
| age | 61.4 ± 1.3 | 63.8 ± 1.0 | 0.15 |
| % male | 75 | 76 | 1 |
| % stable angina | 36 | 36 | 0.9 |
| % unstable angina | 29 | 38 | 0.26 |
| % acute MI | 15 | 13 | 0.3 |
| % s/p MI | 41 | 44 | 0.8 |
| % s/p CABG | 5 | 14 | 0.066 |
| % hypertension | 55 | 59 | 0.74 |
| % diabetes | 21 | 28 | 0.33 |
| % smokers | 52 | 47 | 0.53 |
| % hypercholesterolemia | 60 | 60 | 0.2 |
| number of diseased vessels | 1.9 ± 0.1 | 2.4 ± 0.1 | 0.00001 |

TABLE 5

Characteristics of Patients Segregated by Haptoglobin Phenotype

| | Hp phenotype | | |
|---|---|---|---|
| | 1-1 and 2-1 | 2-2 | p |
| n | 78 | 108 | |
| age | 63.1 ± 1.1 | 62.4 ± 1.2 | 0.58 |
| % male | 77 | 76 | 1 |
| % stable angina | 41 | 33 | 0.35 |
| % unstable angina | 36 | 32 | 0.73 |
| % acute MI | 13 | 16 | 0.73 |
| % s/p MI | 49 | 38 | 0.12 |
| % s/p CABG | 12 | 7 | 0.48 |
| % hypertension | 64 | 52 | 0.13 |
| % diabetes | 24 | 25 | 0.92 |
| % smokers | 46 | 52 | 0.54 |
| % hypercholesterolemia | 62 | 59 | 0.86 |
| number of diseased vessels | 2.1 ± 0.1 | 2.1 ± 0.1 | 0.94 |

Haptoglobin 1 allele dose effect in Diabetic Nephropathy: In a separate study, 9 consecutive patients with type II DM were recruited and analyzed with respect to DN and haptoglobin phenotype as described hereinabove. Although the number of patients is not large enough for a statistical analysis, it appears that the 2-1 phenotype is sufficient to limit the extent of DN to microalbuminuria (Table 6). As in the case type 1 DM (Tables 2 and 7) a 1-1 phenotype seems to prevent DN altogether. The same 53 type I DM patients described hereinabove (Table 2) were similarly analyzed (Table 7). There seems to be a tendency also in this patient group for the 2-1 phenotype to limit the extent of DN to microalbuminuria. Taken together, these data suggest that even one haptoglobin 1 allele is sufficient to offer some degree of protection from oxidative stress to hypoglycemic patients.

TABLE 6

Dose effect of the Hp-1 allele on the development of DN in patients with type II DM

| | Hp phenotype | | |
|---|---|---|---|
| | 1-1 | 2-1 | 2-2 |
| no DN | 3 | 0 | 0 |
| microalbuminuria | 0 | 3 | 0 |
| macroalbuminuria | 0 | 0 | 3 |

TABLE 7

Dose effect of the Hp-1 allele on the development of DN in patients with type I DM

| | Hp phenotype | | |
|---|---|---|---|
| | 1-1 | 2-1 | 2-2 |
| no DN | 12 | 15 | 12 |
| microalbuminuna | 0 | 5 | 4 |
| macroalbuminuria | 0 | 1 | 4 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of evaluating a risk of a diabetic patient to develop a vascular complication selected from the group consisting of diabetic retinopathy, diabetic nephropathy, restenosis after coronary angioplasty and fewer coronary artery collateral blood vessel, the method comprising the step of determining a haptoglobin phenotype of the diabetic patient and thereby evaluating the risk of the diabetic patient to develop vascular complications, wherein the risk is decreased in patients with haptoglobin 1-1 phenotype as compared to patients with haptoglobin 1-2 or haptoglobin 2-2 phenotypes.

2. The method of claim 1, wherein said step of determining said haptoglobin phenotype comprises determining a haptoglobin genotype of the diabetic patient.

3. The method of claim 2, wherein said step of determining said haptoglobin genotype of the diabetic patient comprises a method selected from the group consisting of a signal amplification method, a direct detection method and detection of at least one sequence change.

4. The method of claim 3, wherein said signal amplification method amplifies a molecule selected from the group consisting of a DNA molecule and an RNA molecule.

5. The method of claim 3, wherein said signal amplification method is selected from the group consisting of PCR, LCR (LAR), Self-Sustained Synthetic Reaction (3SR/NASBA) and Q-Beta (Qβ) Replicase reaction.

6. The method of claim 3, wherein said direct detection method is selected from the group consisting of a cycling probe reaction (CPR) and a branched DNA analysis.

7. The method of claim 3, wherein said detection of at least one sequence change employs a method selected from the group consisting of restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis and Dideoxy fingerprinting (ddF).

8. The method of claim 1, wherein said step of determining said haptoglobin phenotype comprises directly determining the haptoglobin phenotype of the diabetic patient.

9. The method of claim 8, wherein said step of determining said haptoglobin phenotype is effected by an immunological detection method.

10. The method of claim 9, wherein said immunological detection method is selected from the group consisting of a radio-immunoassay (RIA), an enzyme linked immunosorbent assay (ELISA), a western blot, an immunohistochemical analysis, and fluorescence activated cell sorting (FACS).

11. The method of claim 1, wherein the vascular complication is diabetic retinopathy.

12. The method of claim 1, wherein the vascular complication is diabetic nephropathy.

13. The method of claim 1, wherein the vascular complication is restenosis after coronary angioplasty.

14. The method of claim 1, wherein the vascular complication is fewer coronary artery collateral blood vessel.

* * * * *

SEQUENCE LISTING (1) GENERAL INFORMATION:

(iii) NUMBER OF SEQUENCES:1

(2) INFORMATION FOR SEQ ID NO:1:

(i) SEQUENCE CHARACTERISTICS:
      (A) LENGTH:21
      (B) TYPE:amino acid
      (C) STRANDEDNESS:single
      (D) TOPOLOGY:linear

```
(xi) SEQUENCE DESCRIPTION: SEQ ID NO:1:

Ala Val Gly Asp Lys Leu Pro Glu Cys Glu Ala Asp Asp Gly Gln
                 5                  10                  15

Pro Pro Pro Lys Cys Ile
                20
```